United States Patent
Cao et al.

(10) Patent No.: US 10,600,159 B2
(45) Date of Patent: Mar. 24, 2020

(54) APPARATUS AND METHOD FOR ENHANCING SPATIAL RESOLUTION OF CT IMAGE AND CT IMAGING SYSTEM

(71) Applicant: General Electric Company, Schenectady, NY (US)

(72) Inventors: Ximiao Cao, Beijing (CN); Xueli Wang, Beijing (CN); Chen Li, Beijing (CN)

(73) Assignee: General Electric Company, Schenectady, NY (US)

( * ) Notice: Subject to any disclaimer, the term of this patent is extended or adjusted under 35 U.S.C. 154(b) by 186 days.

(21) Appl. No.: 15/850,879

(22) Filed: Dec. 21, 2017

(65) Prior Publication Data

US 2018/0182076 A1    Jun. 28, 2018

(30) Foreign Application Priority Data

Dec. 26, 2016   (CN) .......................... 2016 1 1217437

(51) Int. Cl.
*G06T 5/00*  (2006.01)
*G06T 11/00* (2006.01)
*G06T 7/00*  (2017.01)
*A61B 6/03*  (2006.01)
(Continued)

(52) U.S. Cl.
CPC .............. *G06T 5/003* (2013.01); *A61B 6/032* (2013.01); *A61B 6/5205* (2013.01); *G06T 5/20* (2013.01); *G06T 7/0012* (2013.01); *G06T 11/005* (2013.01); *G06T 11/006* (2013.01); *G06T 11/008* (2013.01); *A61B 6/5258* (2013.01); *A61B 6/582* (2013.01);
(Continued)

(58) Field of Classification Search
CPC ..... A61B 6/5205; A61B 6/5258; A61B 6/582; A61B 6/032; G06T 5/003; G06T 11/005; G06T 11/008; G06T 2211/416; G06T 2211/421; G06T 7/0012; G06T 2207/10081; G06T 2210/41; G06T 5/20; G06T 11/006
See application file for complete search history.

(56) References Cited

U.S. PATENT DOCUMENTS 5,864,598 A    1/1999  Hsieh et al.
2006/0067461 A1  3/2006  Yin et al.
(Continued)

FOREIGN PATENT DOCUMENTS

JP    11-000325 A   1/1999
JP    2002-065663 A  3/2002
(Continued)

OTHER PUBLICATIONS

English Translation of JP Office Action for corresponding application 2017-247760; dated Dec. 11, 2018; 6 pages.

*Primary Examiner* — Yon J Couso

(57) ABSTRACT

The present invention provides an apparatus and a method for enhancing spatial resolution of a CT image and a CT imaging system, the method comprising: acquiring an original CT projection curve; performing deconvolution for projection data on the original CT projection curve in a tube sampling direction or a texture direction of the original CT projection curve; and reconstructing an image according to the projection data after deconvolution.

13 Claims, 3 Drawing Sheets

(51) Int. Cl.
*G06T 5/20* (2006.01)
*A61B 6/00* (2006.01)
(52) U.S. Cl.
CPC ........................ *G06T 2207/10081* (2013.01); *G06T 2210/41* (2013.01); *G06T 2211/416* (2013.01); *G06T 2211/421* (2013.01)

(56) References Cited

U.S. PATENT DOCUMENTS

| | | | | |
|---|---|---|---|---|
| 2007/0140408 | A1* | 6/2007 | Takiura | A61B 6/032 378/4 |
| 2010/0053203 | A1* | 3/2010 | Bernhardt | A61B 6/032 345/617 |
| 2014/0211925 | A1* | 7/2014 | Dong | A61B 6/585 378/207 |
| 2015/0036902 | A1* | 2/2015 | Zamyatin | G06T 7/0012 382/131 |

FOREIGN PATENT DOCUMENTS

| | | |
|---|---|---|
| JP | 2004-024659 A | 1/2004 |
| JP | 2014-087635 A | 5/2014 |
| JP | 2015-029913 A | 2/2015 |

* cited by examiner

APPARATUS AND METHOD FOR ENHANCING SPATIAL RESOLUTION OF CT IMAGE AND CT IMAGING SYSTEM

FIELD

The present invention relates to the field of medical imaging, and more particularly to a CT imaging system and an apparatus and a method for enhancing spatial resolution of a CT image.

BACKGROUND

Spatial resolution is an important indicator for measuring image quality in Tomography (CT) imaging technology. The spatial resolution may reflect the minimum limit of geometric dimensions of objects that can be recognized in an image. Therefore, theoretically speaking, the higher the spatial resolution is, the better the image quality will be. However, in the actual CT imaging system, the spatial resolution is affected by multiple factors such as focal spot size, reconstruction kernel, detector size and the like.

To enhance the spatial resolution, the traditional method is adjusting the convolution kernel in the reconstruction. A high-pass convolution kernel better preserves the high resolution of an image, but brings greater noise. A low-pass convolution kernel better suppresses the noise, but the resolution is limited. The convolution kernel plays a role of balancing the noise and the resolution. However, the high-pass of a convolution kernel has frequency limitation. When it is higher than a certain frequency, a further resolution increase will instead induce greater noise, and more artifacts, while the limit frequency of a system is limited by the detector size and the way of sampling.

Another method for enhancing the spatial resolution is filtering in a direction of a detector channel, which is mainly used to solve a boundary blur caused by the secondary scattering of the tube in the system.

However, none of the above methods can solve an image blur caused by the coupling of the adjacent sampling views for the same detector channel.

Thus, the present invention is intended to explore the coupling relationship between data views: that is, for a certain detector, there is a repeated area across which the ray beams scan, between the adjacent views. The enhanced filtering in the view direction of the present invention is just to remove the coupling relationship of this part, and thereby solve the blurring problem caused in the view direction.

SUMMARY

One object of the present invention is to provide a novel apparatus and method for enhancing spatial resolution of a CT image and a CT imaging system, which can enhance spatial resolution of a CT image.

Exemplary embodiments of the present invention provide a method for enhancing spatial resolution of a CT image, comprising: acquiring an original CT projection curve; performing deconvolution for projection data on the original CT projection curve in a tube sampling direction or a texture direction of the original CT projection curve; and reconstructing an image according to the projection data after deconvolution.

Exemplary embodiments of the present invention also provide an apparatus for enhancing spatial resolution of a CT image, comprising: an original data acquisition module for acquiring an original CT projection curve; a deconvolution processing module for performing deconvolution for projection data on the original CT projection curve in a tube sampling direction or a texture direction of the original CT projection curve; an image reconstruction module for reconstructing an image according to the projection data after deconvolution.

Exemplary embodiments of the present invention further provide a CT imaging system comprising the above apparatus for enhancing spatial resolution of a CT image.

Other features and aspects will be apparent through the following detailed description, figures and claims.

BRIEF DESCRIPTION OF THE DRAWINGS

The present invention can be better understood in light of the description of exemplary embodiments of the present invention with reference to the accompanying drawings, in which.

DETAILED DESCRIPTION

Figure 1:
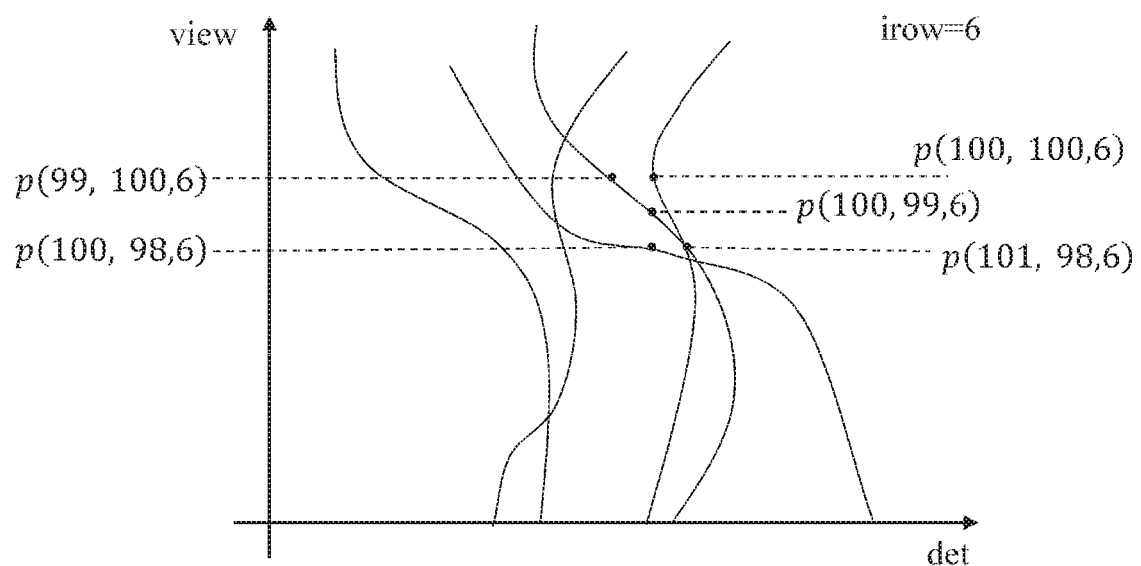
FIG. 1 is an exemplary schematic diagram of original CT projection curves.

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present application for invention do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

An embodiment of the present invention provides a CT imaging system that may comprise a rotational gantry and an image processing system. The rotational gantry is of a hollow structure so as to be capable of receiving a human body to be detected, where a tube and a detector are disposed oppositely inside the rotational gantry, and the rotational gantry can drive the tube and the detector to rotate around the detected human body. The tube is used to emit X-rays to the detected human body during the rotation of the rotational gantry, and the X-rays can penetrate the human body so as to be collected by the detector. The X-rays collected by the detector are converted to image signals after being processed. The image processing system is used to receive the image signals as the original CT projection data for data processing, so as to obtain the tomography image of the detected human body.

The above original CT projection data may also be referred to as an original CT projection curve, such as a sinogram commonly understood by the person skilled in the art. FIG. 1 is an exemplary schematic diagram of original CT projection curves. As shown in FIG. 1, the original CT projection curves are two-dimensional curves with the detector channel direction and the tube sampling direction as the dimensions, where each point on the curves corresponds to a certain view (representing the tube collecting direction or scanning angle) or a projection value received on a certain detector channel. The original CT projection data, original CT projection curves and the like are all well known technologies in the art, and thus will not be described in details.

Figure 2:
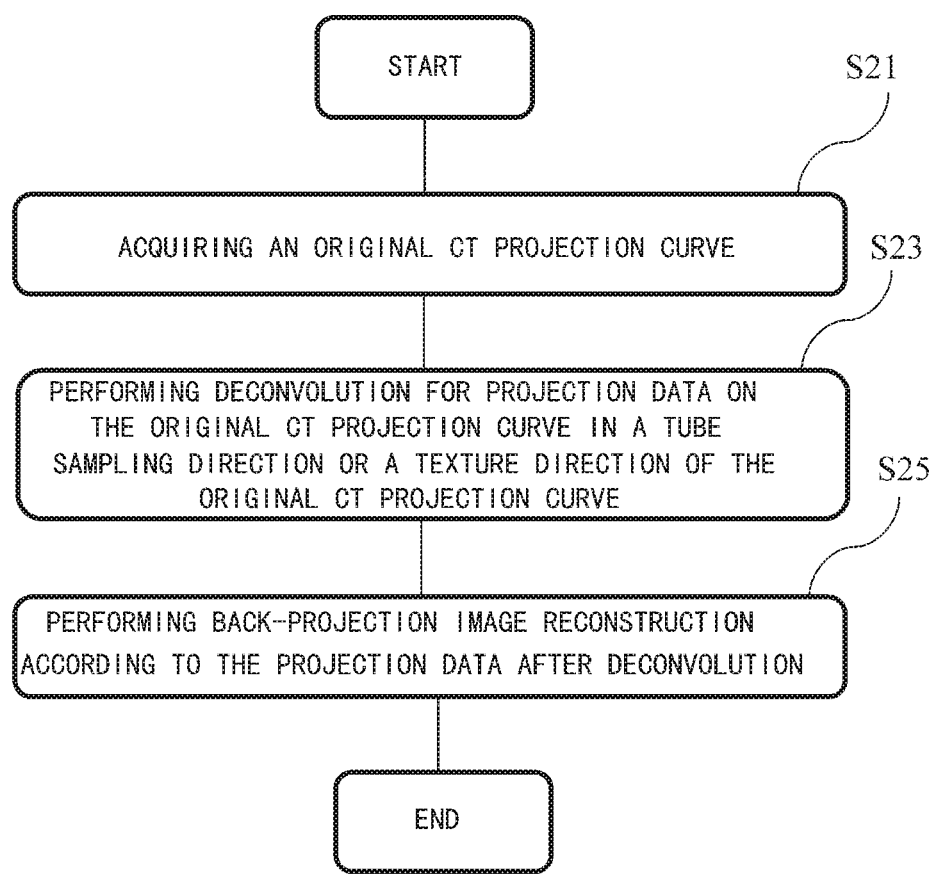
FIG. 2 is a flowchart of a method for enhancing spatial resolution of a CT image provided by one exemplary embodiment of the present invention.

FIG. 2 is a flowchart of a method for enhancing the spatial resolution of a CT image provided by one embodiment of the present invention. The method may be used to process the projection data on the original projection curve in FIG. 1, so as to obtain higher resolution when image reconstruction is performed according to the processed data.

As shown in FIG. 2, the method for enhancing the spatial resolution of a CT image may comprise Step S21, Step S23 and Step S25.

In Step S21, an original CT projection curve is acquired. In Step S23, deconvolution is performed for projection data on the original CT projection curve in the tube sampling direction or the texture direction of the original CT projection curve. In Step S25, an image is reconstructed according to the projection data after deconvolution.

The above tube sampling direction, that is, the "view" commonly understood by the person skilled in the art, refers to that, as the tube can emit X-rays from different scanning views when it is rotating with the rotational gantry, such that there are different tube sampling directions at the time of interval sampling. Acquiring image signals in two adjacent tube sampling directions may possibly cause a blurring phenomenon of the finally reconstructed image due to signal tailing, overlapping and the like. In order to reduce or remove the problem of low resolution in the tube sampling direction, in Step S23, deconvolution may be performed for the projection data on the original CT projection curve in the tube sampling direction, or in the texture direction of the projection curve.

Figure 3:
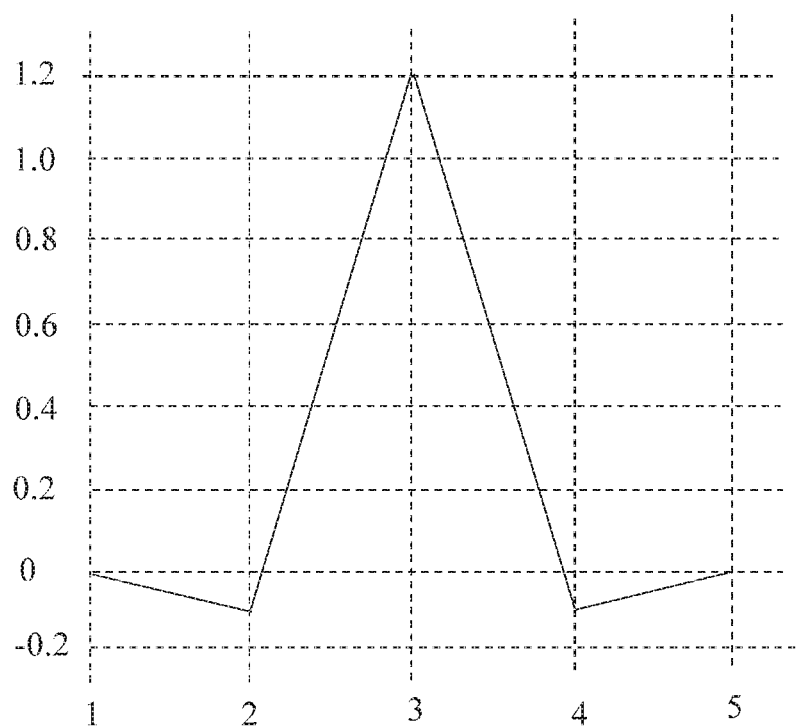
FIG. 3 exemplarily illustrates a convolution kernel model used in a deconvolution operation performed on projection data in one embodiment of the present invention.

FIG. 3 exemplarily illustrates a convolution kernel model used in a deconvolution operation on projection data in one embodiment of the present invention. As shown in FIG. 3, the convolution kernel is an enhanced convolution kernel, that is, in Step S23, deconvolution is further performed for the projection data on the original CT projection curve through the enhanced convolution kernel.

The above convolution kernel is a pre-set empirical value. For example, the convolution kernel may be a matrix, whose length is determined by the size characteristics of the detector, and the amplitude difference of the elements in the matrix is determined according to the degree of enhancement for the spatial resolution of the image. Corresponding relationships between convolution kernels of different element values and spatial resolutions as well as noise may be obtained through a large number of experiments, and a convolution kernel corresponding to a higher spatial resolution and a lower noise is finally chosen.

Furthermore, a sum of the above convolution kernels is equal to 1, that is, the sum of the element values in the matrix is 1. In this way, the over-drift of the CT value of the image caused by over adjustment on the CT value of the image is avoided.

Optionally, in Step S23, deconvolution may be performed for the projection data on the original CT projection curve according to the following equation (1):

$$p'(idet, iview, irow) = \Sigma_{j=-n}^{j=n} p(idet, iview+j, irow) * kernel(j+n+1) \quad (1)$$

where p' is the projection data after deconvolution, p is the projection data on the original CT projection curve, idet is a coordinate value in the detector channel direction, iview is a coordinate value in the tube sampling direction, irow is a coordinate value in the layer-scanning direction, n is a predetermined natural number, kernel is a convolution kernel, and the length of the convolution kernel is $2*n+1$.

Taking the original projection data in FIG. 1 and the convolution kernel in FIG. 3 as an example to illustrate, for example, in FIG. 3, n is 1, the length of the convolution kernel is 3, the convolution kernel is [−0.1, 1.2, −0.1], where kernel1 is −0.1, kernel2 is 1.2 and kernel3 is −0.1, and their summation is 1 (−0.1+1.2−0.1=1). Assuming irow=6, idet=100, iview=99, when convolution operation is performed along the view direction (vertical axis) in FIG. 1 so as to obtain a CT value of the pixel of the 100th channel, 99th collecting angle of the $6^{th}$ column of detectors, it may be calculated by the following equation:

$$p'(100,99,6) = p(100,98,6)*(-0.1) + p(100,99,6)*1.2 + p(101,98,6)*(-0.1).$$

When the convolution operation is performed along the texture direction of the curve (flow direction of the curve) in FIG. 1 so as to obtain a CT value p'(100, 99, 6) of the pixel of the $100^{th}$ channel, $99^{th}$ collecting angle of the $6^{th}$ column of detectors, it may be calculated by the following equation:

$$p'(100,99,6) = p(99,100,6)*(-0.1) + p(100,99,6)*1.2 + p(101,100,6)*(-0.1).$$

The person skilled in the art should understand that CT imaging may include the following procedures: pre-processing, image reconstruction, and post-processing. The pre-processing comprises performing processing, such as channel calibration, dark current calibration, beam hardening calibration and the like, on the original CT projection data. The image reconstruction comprises convolution filtering in frequency domain and back-projection and the like on the above calibrated data. The post-processing comprises performing processing, such as artifact-removing and the like, on the reconstructed image.

The original CT projection curve acquired in the above Step S21 may be data without being pre-processed, or data processed by at least one pre-processing, that is, Step S23 may be performed before the pre-processing stage, or may be performed in the pre-processing stage, for example, Step S23 may serve as an intermediate step or a last step of the pre-processing stage. Step S25 may be performed in the image reconstruction stage. In this stage, the above data after deconvolution may go through at first convolution filtering in the frequency domain, and then back-projection.

Therefore, Step S25 may comprise performing back-projection for the projection data after deconvolution, and may further comprise: performing convolution filtering for the projection data after deconvolution in the frequency domain before back-projection.

Figure 4:
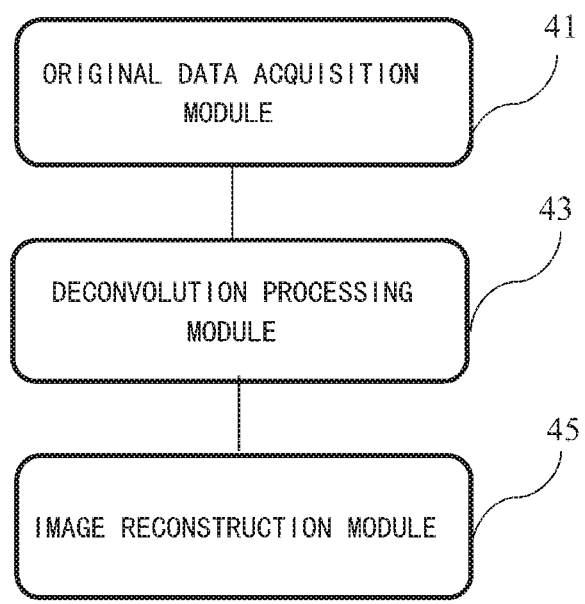
FIG. 4 is a block diagram of an apparatus for enhancing spatial resolution of a CT image provided by one embodiment of the present invention.

FIG. 4 is a block diagram of an apparatus for enhancing spatial resolution of a CT image provided by one embodiment of the present invention. As shown in FIG. 4, the apparatus comprises an original data acquisition module 41, a deconvolution processing module 43, and an image reconstruction module 45. The original data acquisition module 41 is used for acquiring an original CT projection curve. The deconvolution processing module 43 is used for performing deconvolution for the projection data on the original CT projection curve in the tube sampling direction or the texture direction of the original CT projection curve. The image reconstruction module 45 is used for reconstructing an image according to the projection data after deconvolution.

Optionally, the above deconvolution processing module 43 performs deconvolution for the projection data on the original CT projection curve through an enhanced convolution kernel. Optionally, the convolution kernel is a pre-set empirical value, and a sum of the convolution kernels is equal to 1.

Specifically, the deconvolution processing module 43 performs deconvolution for the projection data on the original CT projection curve according to the above Equation (1).

Optionally, the image reconstruction module 45 comprises a back-projection unit for performing back-projection on the projection data after deconvolution.

Optionally, the image reconstruction module 45 further comprises a filtering unit, for performing convolution filtering for the projection data after deconvolution in the frequency domain before back-projection.

The CT imaging system according to the embodiment of the present invention may comprise the above apparatus for enhancing spatial resolution of a CT image, and in particular, the apparatus for enhancing spatial resolution of a CT image may be disposed in the above image processing system of the CT imaging system.

In the traditional method, in the process of image reconstruction, convolution filtering in the frequency domain and back-projection are directly performed on the pre-processed original CT projection data; the spatial resolution is improved by selecting a convolution kernel, however, as limited by the limit frequency of the detector, when the spatial resolution achieves the limit, if convolution filtering in the frequency domain is further performed, the spatial resolution will instead be submerged by the increased noise. In the embodiment of the present invention, deconvolution is at first performed on the original data in the tube sampling direction, so that signal tailing, overlapping and the like in the tube sampling direction are corrected in the original data before back-projection, so as to perform back-projection based on more accurate original data when the image reconstruction is being performed, and eventually obtain a CT image with a higher spatial resolution in the tube sampling direction. By test, comparing with the traditional method, the embodiment of the present invention can improve the spatial resolution by at least 1p/cm, and have a higher signal-to-noise ratio.

Although some exemplary embodiments have been described as mentioned above, it should be understood that various modifications may still be made. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the Claims.

What is claimed is:

1. A method for enhancing spatial resolution of a CT image, comprising:
    acquiring an original CT projection curve;
    performing deconvolution for projection data on the original CT projection curve in a tube sampling direction or a texture direction of the original CT projection curve; and
    reconstructing an image according to the projection data after deconvolution;
    wherein deconvolution is performed for the projection data on the original CT projection curve according to the following equation:

$$p'(idet, iview, irow) = \sum_{j=-n}^{j=n} p(idet, iview + j, irow) * \text{kernel}(j + n + 1)$$

where p' is the projection data after deconvolution, p is the projection data on the original CT projection curve, idet is a coordinate value in a detector channel direction, iview is a coordinate value in the tube sampling direction, irow is a coordinate value in a layer scanning direction, kernel is the convolution kernel, and n is a predetermined natural number.

2. The method for enhancing spatial resolution of a CT image according to claim 1, wherein deconvolution is performed for the projection data on the original CT projection curve through an enhanced convolution kernel.

3. The method for enhancing spatial resolution of a CT image according to claim 2, wherein the convolution kernel is a pre-set empirical value.

4. The method for enhancing spatial resolution of a CT image according to claim 3, wherein a sum of the convolution kernels is equal to 1.

5. The method for enhancing spatial resolution of a CT image according to claim 1, wherein reconstructing an image according to the projection data after deconvolution comprises: performing back-projection for the projection data after deconvolution.

6. The method for enhancing spatial resolution of a CT image according to claim 5, wherein reconstructing an image according to the projection data after deconvolution further comprises: performing convolution filtering for the projection data after deconvolution in a frequency domain before the back-projection.

7. An apparatus for enhancing spatial resolution of a CT image, comprising:
    an original data acquisition module for acquiring an original CT projection curve;
    a deconvolution processing module for performing deconvolution for projection data on the original CT projection curve in a tube sampling direction or a texture direction of the original CT projection curve; and an image reconstruction module for reconstructing an image according to the projection data after deconvolution;

wherein the deconvolution processing module performs deconvolution for the projection data on the original CT projection curve according to the following equation:

$$p'(idet, iview, irow) = \sum_{j=-n}^{j=n} p(idet, iview + j, irow) * \text{kernel}(j + n + 1)$$

where p' is the projection data after deconvolution, p is the projection data on the original CT projection curve, idet is a coordinate value in a detector channel direction, iview is a coordinate value in the tube sampling direction, irow is a coordinate value in a layer scanning direction, kernel is the convolution kernel, and n is a predetermined natural number.

8. The apparatus for enhancing spatial resolution of a CT image according to claim 7, wherein the deconvolution processing module performs deconvolution for the projection data on the original CT projection curve through an enhanced convolution kernel.

9. The apparatus for enhancing spatial resolution of a CT image according to claim 8, wherein the convolution kernel is a pre-set empirical value.

10. The apparatus for enhancing spatial resolution of a CT image according to claim 9, wherein a sum of the convolution kernels is equal to 1.

11. The apparatus for enhancing spatial resolution of a CT image according to claim 7, wherein the image reconstruction module comprises a back-projection unit for performing back-projection for the projection data after deconvolution.

12. The apparatus for enhancing spatial resolution of a CT image according to claim 11, wherein the image reconstruction module comprises a filtering unit for performing convolution filtering for the projection data after deconvolution in a frequency domain before the back-projection.

13. A CT imaging system, comprising the apparatus for enhancing spatial resolution of a CT image according to claim 7.

* * * * *